US009598429B2

(12) United States Patent
Fu et al.

(10) Patent No.: US 9,598,429 B2
(45) Date of Patent: Mar. 21, 2017

(54) METHOD FOR SYNTHESIZING MILBEMYCIN OXIME

(71) Applicant: HUBEI HONCH PHARMACEUTICAL CO.,LTD, Huanggang (CN)

(72) Inventors: Guangming Fu, Huanggang (CN); Fubiao He, Huanggang (CN); Wenkai Zhang, Huanggang (CN)

(73) Assignee: HUBEI HONCH PHARMACEUTICAL CO., LTD, Huanggang (CN)

( * ) Notice: Subject to any disclaimer, the term of this patent is extended or adjusted under 35 U.S.C. 154(b) by 0 days.

(21) Appl. No.: 15/239,819

(22) Filed: Aug. 17, 2016

(65) Prior Publication Data

US 2017/0050977 A1 Feb. 23, 2017

(30) Foreign Application Priority Data

Aug. 20, 2015 (CN) .......................... 2015 1 0513971

(51) Int. Cl.
*C07D 493/22* (2006.01)

(52) U.S. Cl.
CPC .................................. *C07D 493/22* (2013.01)

(58) Field of Classification Search
CPC .................................................... C07D 493/22
See application file for complete search history.

(56) References Cited

PUBLICATIONS

PubChem. "Chlorite." © 2016. Available from: < https://pubchem.ncbi.nlm.nih.gov/compound/chlorite#section=Top >.*
PubChem. "Hypochlorite." © 2016. Available from: < https://pubchem.ncbi.nlm.nih.gov/compound/Hypochlorite#section=Top >.*
PubChem. "Pyridine." © 2016. Available from: < https://pubchem.ncbi.nlm.nih.gov/compound/pyridine#section=Top >.*
PubChem. "Piperidine." © 2016. Available from: < https://pubchem.ncbi.nlm.nih.gov/compound/piperidine#section=Top >.*

* cited by examiner

*Primary Examiner* — Noble Jarrell
*Assistant Examiner* — John S Kenyon
(74) *Attorney, Agent, or Firm* — Gokalp Bayramoglu

(57) ABSTRACT

The present invention provides a method for synthesizing Milbemycin oxime. The method comprises the following steps. (1) Oxidizing reaction: oxidizing Milbemycin, using hypochlorite or chlorite as oxidizers and piperidine nitrogen oxygen free radicals as the catalyst and halide as the catalyst promoter. The oxidation reaction is conducted in a dichloromethane solvent for 0.5-4 hours at −5-15° C. to produce the intermediate product Milbemycin ketone. (2) Oximation reaction: reacting the Milbemycin ketone with a hydroxylamine hydrochloride oximation agent in a 1,4-dioxane reaction solvent for 10-16 hours at 25-35° C. to obtain Milbemycin oxime. The method provided by the present invention realized the industrial production of Milbemycin oxime for the first time domestically. Moreover, the yield of the prepared product is higher than competing products both at home and abroad.

6 Claims, 4 Drawing Sheets

METHOD FOR SYNTHESIZING MILBEMYCIN OXIME

TECHNICAL FIELD

The present invention relates to the field of chemical substance synthesizing, particularly relates to a method for synthesizing Milbemycin oxime which is a vermifuge of the type of semi-synthesis macrocyclic lactones.

BACKGROUND

Milbemycin oxime is a vermifuge of the type of semi-synthetic macrocyclic lactones, and is the oxime derivative of Milbemycins A3 and A4. Milbemycin oxime has the broad-spectrum effect of anti-parasitic. It has a good anti-parasitic effect against endoparasite, ectoparasite, especially nematode and arthropod. Lee et al's research of the mechanism of neuropharmacology of Milbemycin oxime on the vitro activity of Guangdong blood Strongylid and dog Dirofilaria shows that the inhibition and stimulation effects of Milbemycin oxime to the two types of parasites is performed by the gabergic and cholinergic mechanism. The drug combines with the locus on the target parasite cell with high specificity and affinity, affecting the permeability of the cytomembrane with respect to Cl—. Then, the releasing amount of γ-aminobutyric acid (GABA), which is an inhibitory neurotransmitter for the neurocyte of nematode and the myocyte of arthropod, increases. The Cl— channel controlled by glutamic acid opens. The permeability of the neurilemma with respect to Cl— is improved. GABA takes effect on the presynaptic nerve endings, decreasing the releasing of the excitatory transmitter, such that the subsynaptic membrane generates a weakened excitatory postsynaptic potential (EPSP). Since the depolarization of the membrane potential cannot reach the threshold, the postsynaptic neuron cannot enter the excitatory state, so as to cause inhibition. Thus, the parasite is paralyzed and dead. The main peripheral neurotransmission media of mammalia is acetyl choline, which will not be affected. Though this type of drug has a certain effect on GABA in central nervous system of the brain, it is not likely to pass through the Blood Brain Barrier. Thus, if used in a remanded dosage, it has no toxic or side effect on the vertebrate. After entering the body of a mammal, this type of drug rarely distributes among the brain tissue of the mammal. Thus, it can take effect on ectoparasite and endoparasite selectively, without affecting the animal host.

Literature reports of Milbemycin oxime mainly focus on the fermentation and strain breeding of Milbemycins. Literature reports of synthesizing Milbemycin oxime are rare. CN103896961A discloses a method for preparing a compound of the type of Milbemycin oxime. This method uses pyridinium chlorochromate as the oxidizer to conduct the oxidizing reaction. There are a lot of side reactions. The yield is low. Moreover, chromium trioxide used in the procedure is toxic, which is likely to cause heavy metal pollution.

SUMMARY

The present invention solves the problem in the prior art and provides a method for synthesizing Milbemycin oxime. This method realized the industrial production of Milbemycin oxime for the first time domestically. Moreover, the yield of the prepared product is higher than competing products both at home and abroad. The present invention uses hypochlorite as the oxidizer, and uses piperidine nitrogen oxygen free radicals as the catalyst. The condition is mild and side reactions are reduced. The cost is low, with high yield.

The technical solution which achieves the above purpose of the present invention is:

A method for synthesizing Milbemycin oxime, wherein the method comprises following steps:

(1) Oxidizing reaction: using Milbemycins as raw material, which has a structural formula as follows:

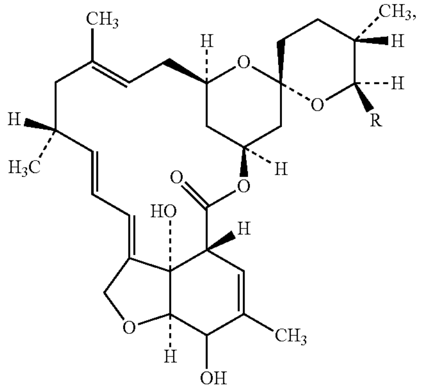

hypochlorite or chlorite is used as an oxidizer. Piperidine nitrogen oxygen free radical is used as the catalyst. Halide is used as the catalyst promoter. The reaction is conducted in a dichloromethane solvent for 0.5-4 hours at −5-15° C. The reaction product is post-processed to obtain an intermediate product Milbemycin ketone, which has a structural formula as follows:

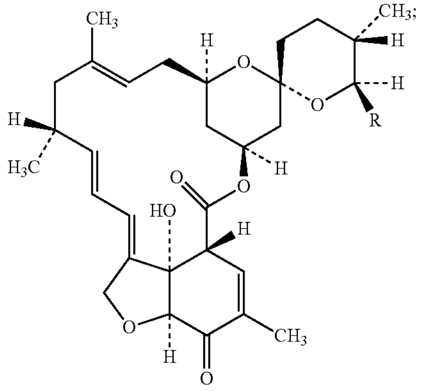

(2) Oximation reaction: methyl alcohol and 1,4-dioxane are used as the reaction solvent. Hydroxylamine hydrochloride is used as an oximation agent. The reaction is conducted for 10-16 hours at 25-35° C. After post-processed and purified, Milbemycin oxime is obtained, which has a structural formula as follows:

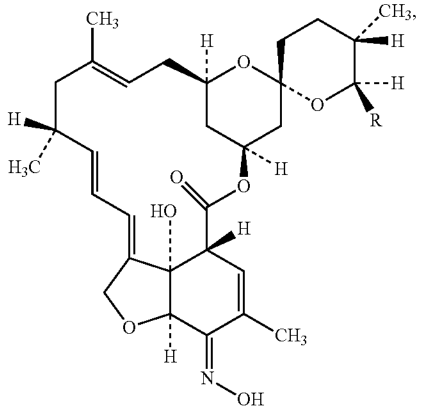

wherein R is methyl or ethyl.

The catalyst used in step (1) is one of 2,2,6,6-tetramethylpiperidide-N-oxyl, 4-hydroxy-2,2,6,6-tetramethylpiperidide-N-oxyl, 4-methoxy-2,2,6,6-tetramethylpiperidide-N-oxyl, 4-acetyl 2,2,6,6-tetramethylpiperidide-N-oxyl, and 4-azyl-2,2,6,6-tetramethylpiperidide-N-oxyl. The mole ratio of the catalyst and Milbemycins is 0.05-0.4:1.

The oxidizer used in step (1) is one of sodium hypochlorite, calcium hypochlorite, and sodium chlorite, a mole ratio of oxidizer and Milbemycins is 3.5-3.5:1. The oxidizer is dissolved into a solution by saturated sodium bicarbonate solution. The mass percent concentration of the oxidizer in the solution is 0.5%-10%. The pH value of the solution is controlled in a range of 8.5-11.5. The solution is added dropwise into the raction solution in 4-8 batches. The dropwise interval between each batch is 10-20 min.

The catalyst promoter used in step (1) is one of potassium iodide, sodium bromide, and sodium chloride. The mole ratio of catalyst promoter and Milbemycins is 0.05-0.4:1.

The post-process in step (1) specifically is: first a sodium thiosulfate solution is used to quench the reaction. Next, methyl alcohol is added. The solution is kept still for stratification. The organic phase is dried by anhydrous magnesium sulfate. After being centrifuged under a reduced pressure, it is evaporated to obtain an intermediate product Milbemycin ketone. The mole ratio of sodium thiosulfate and Milbemycins is 10-35:1. The amount of methyl alcohol added is 10-30% of total volume of the reaction system.

In step (2), a mass ratio of oximation agent hydroxylamine hydrochloride and Milbemycins is 1-1.5:1. In the reaction solvent, a mass-to-volume ratio of methyl alcohol and 1,4-dioxane and Milbemycins is, methyl alcohol:1,4-dioxane:Milbemycins=(8-12 L):(10-16 L):1 Kg.

Compared with the prior art, the present invention has the following advantages. 1. The present invention uses hypochlorite as the oxidizer, and uses piperidine nitrogen oxygen free radicals as the catalyst. The condition is mild. Side reactions are reduced. The yield is high and cost is low. Thus, industrial production can be realized. 2. The conversion rate of the product prepared in the present invention is as high as 91%, which is significantly higher than competing products both at home and abroad.

DETAILED DESCRIPTION

Hereinafter, the present invention is described in detail, accompanied by the Figures and specific embodiments. However, the scope of the present invention is not limited to the following embodiments.

Figure 1:
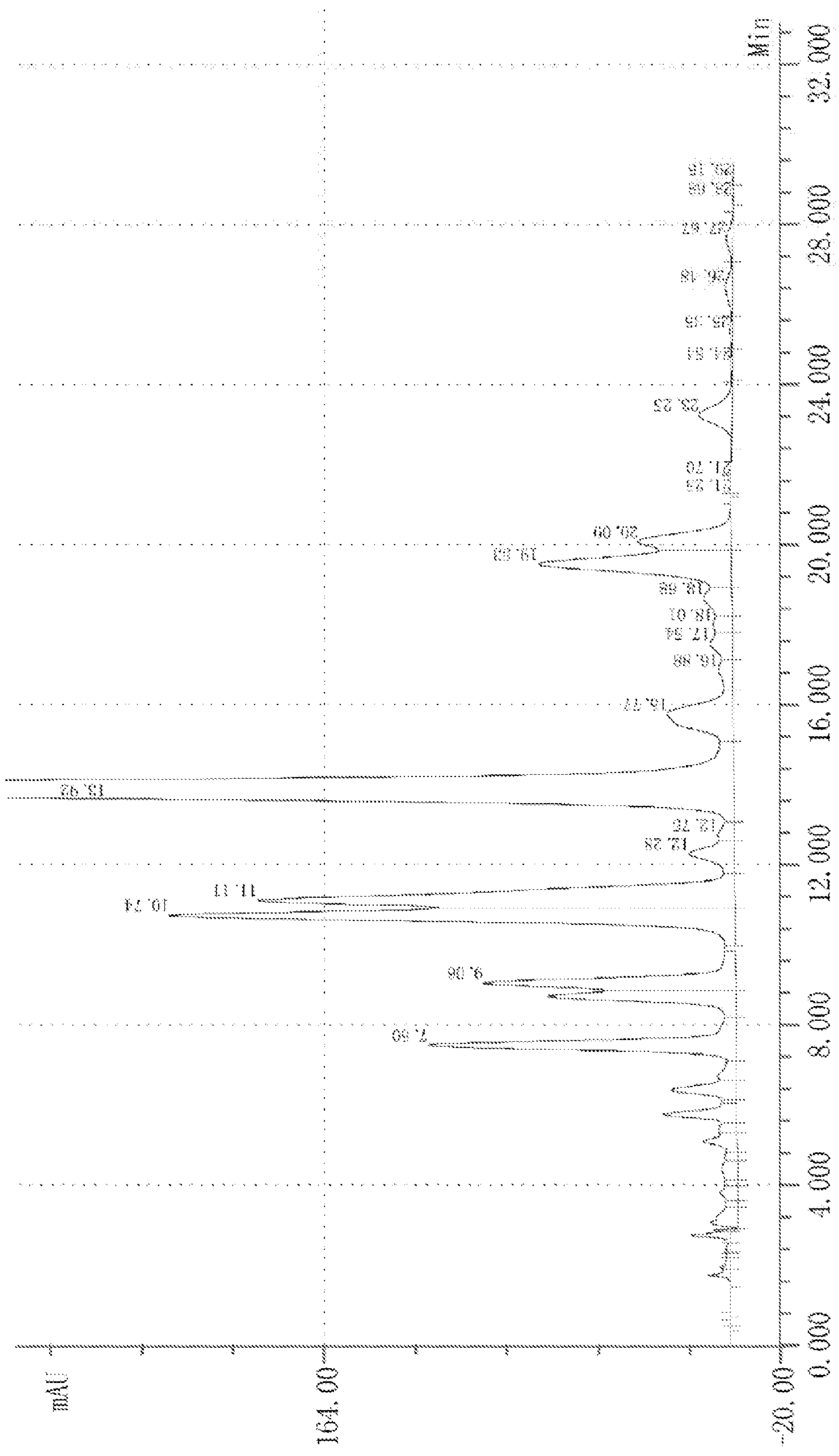
FIG. 1 is a spectogram of Milbemycins used in Embodiment One of the present invention detected by liquid chromatography.

Embodiment One (1) 24.7 Kg of raw material which is demarcated as containing 5 Kg of Milbemycins ($C_{31}H_{43}O_7$ and/or $C_{32}H_{45}O_7$) is put into the reactor. The spectogram of Milbemycins used in the present embodiment detected by liquid chromatography is shown in FIG. 1. In FIG. 1, the peak at 11.11 min is Milbemycins $A_3$ ($C_{31}H_{43}O_7$), and the peak at 13.92 min is Milbemycins $A_4$ ($C_{32}H_{45}O_7$).

300 g of 2,2,6,6-tetramethyl-N-oxyl is added into the reactor. 100 L of dichloromethane is added to dissolve it. The temperature of refrigeration equipment is set to 5° C. The refrigeration and the stirring are turned on. 200 g of sodium bromide is dissolved by 1000 ml of deionized water, and is added into the above reaction solution.

(2) 3.57 Kg of sodium bicarbonate and 11.76 Kg of sodium carbonate are dissolved in 100 L of water. 81 Kg of 20% sodium hypochlorite solution is added and stirred evenly. The pH is adjusted to 10±0.5.

(3) Oxidizer solution is equally divided into five batches, and each batch is added dropwise into the reaction solution. Dropping time for each batch is 20 min. After each batch is added dropwise completely, the interval between each batch is 15 min. After the dropping finishes, the reaction lasts for 1 h.

(4) The preparation of sodium thiosulfate solution: 53 Kg of sodium thiosulfate is dissolved by 200 L of deionized water.

Figure 2:
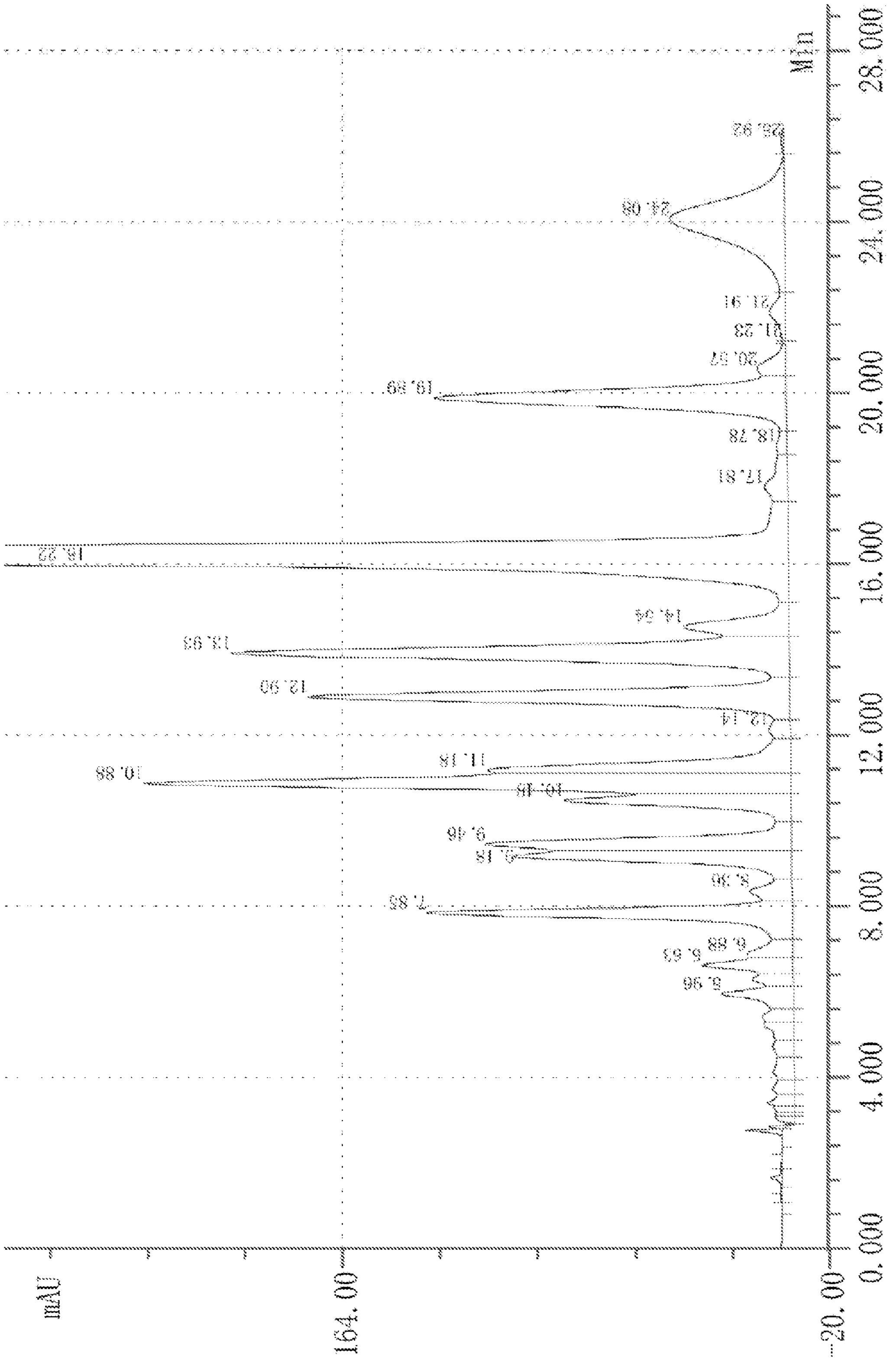
FIG. 2 is a spectogram of Milbemycin ketone intermediate prepared in Embodiment One of the present invention detected by liquid chromatography.

(5) Sample testing. After raw materials react completely, the above sodium thiosulfate solution is added into the reaction system to quench the reaction. Next, 80 L of methyl alcohol is added and stirred evenly. Then, the solution is kept still for 30 min. Liquid separation is conducted. Next, the aqueous phase is extracted using 60 L of dichloromethane. Organic phases are combined. 10 Kg of anhydrous magnesium sulfate is added into the organic phase. It is stirred and dried for 15 min, and is centrifugally filtered. The filtrate is dried by distillation under 50° C. and a reduced pressure. Milbemycin ketone intermediate is obtained. The prepared Milbemycin ketone intermediate, detected by liquid chromatography spectrogram is shown in FIG. 2. In FIG. 2, peak at 12.90 min is Milbemycin $A_3$ ketone. The peak at 16.22 min is Milbemycin $A_4$ ketone.

(6) The Milbemycin ketone intermediate in Embodiment One is dissolved in 50 L of methyl alcohol and 60 L of 1,4-dioxane. The solution is transferred to the reactor. The stirring is turned on.

(7) The preparation of hydroxylamine hydrochloride water solution: 6 Kg of hydroxylamine hydrochloride is dissolved in 10 L of deionized water. The hydroxylamine hydrochloride solution is added dropwise into the reactor, continuing stirring and reacting for 10-16 hours.

(8) Sample testing. After the reaction is completed, the reaction system is dried by distillation at 50° C. under a reduced pressure.

(9) The concentrate is dissolved by 80 L of dichloromethane, and is transferred to the extraction kettle. 40 L of deionized water is added. It is stirred for 15 min. The solution is kept still for 30 min. The liquid separation is conducted. Next, the aqueous phase is extracted again by adding 40 L of dichloromethane. Organic phases are combined. 10 Kg of anhydrous magnesium sulfate is added into the organic phase. It is stirred for 10 min, and is centrifugal filtered. The filtrate is dried by distillation at45-55° C. and under the reduced pressure. 22.6 Kg of the crude product of Milbemycin oxime is obtained. The content of Milbemycin oxime is demarcated as 20.04% by external standard method. The synthesizing yield iz 90.6%.

Figure 3:
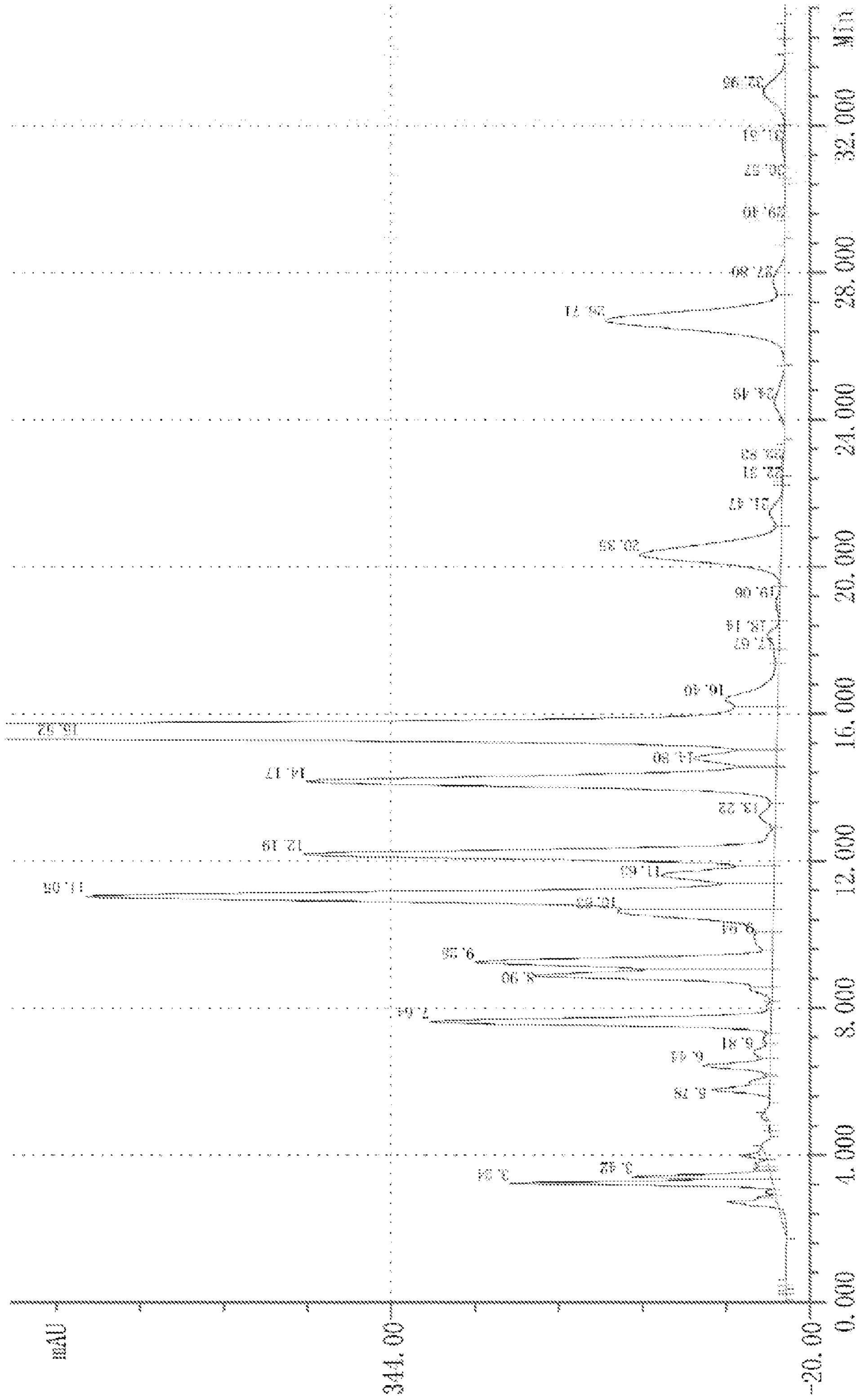
FIG. 3 is a spectrogram of Milbemycin oxime prepared in Embodiment One of the present invention detected by liquid chromatography.

The spectrogram of the crude product of Milbemycin oxime prepared in the present embodiment detected by liquid chromatography is shown in FIG. 3. In FIG. 3, the peak at 12.19 min is Milbemycin oxime $A_3$, and the peak at 15.52 min is Milbemycin oxime $A_4$.

Figure 4:
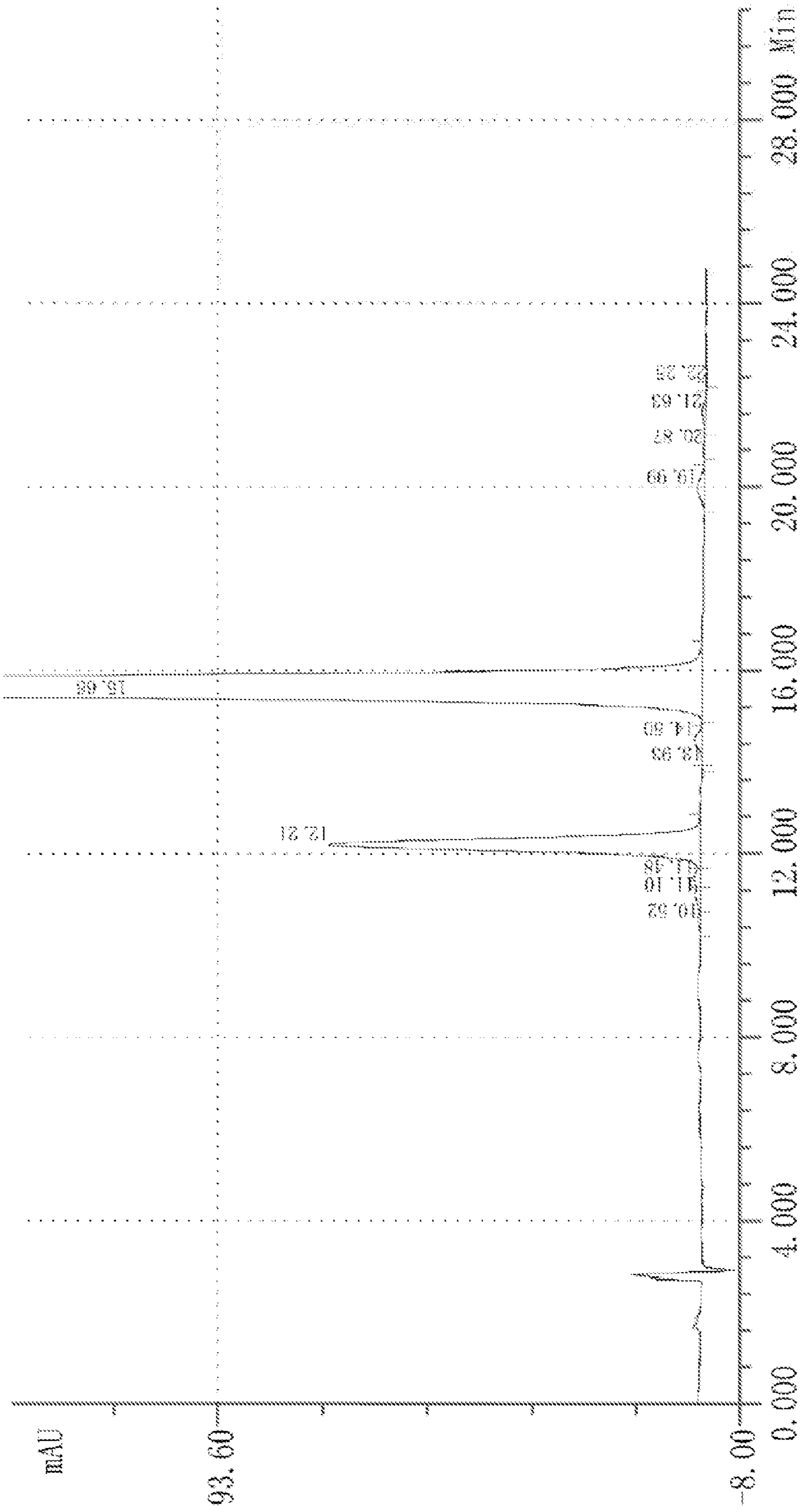
FIG. 4 is a spectrogram of USP control of Milbemycin oxime detected by liquid chromatography.

FIG. 4 is a spectrogram of USP control of Milbemycin oxime detected by liquid chromatography. In FIG. 4, the peak at 12.21 min is Milbemycin oxime $A_3$, and the peak at 15.66 min is Milbemycin oxime $A_4$.

What is claimed is:

1. A method for synthesizing Milbemycin oxime, wherein the method comprises the following steps:

(1) oxidizing reaction: oxidizing Milbemycin

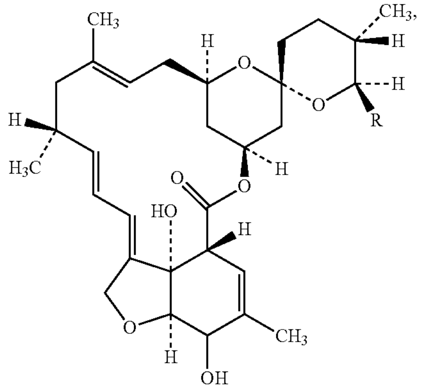

using hypochlorite or chlorite as oxidizers and piperidine nitrogen oxygen free radicals as a catalyst, wherein the catalyst is selected from the group consisting of 2,2,6,6-tetramethylpiperidide-N-oxyl, 4-hydroxy-2,2,6,6-tetramethylpiperidide-N-oxyl, 4-methoxy-2,2,6,6-tetramethylpiperidide-N-oxyl, 4-acetyl 2,2,6,6-tetramethylpiperidide-N-oxyl, and 4-azyl-2,2,6,6-tetramethylpiperidide-N-oxyl, and halide as a catalyst promoter, wherein the oxidation reaction is conducted in a dichloromethane solvent for 0.5-4 hours at −5-15*C, to produce an intermediate product Milbemycin ketone

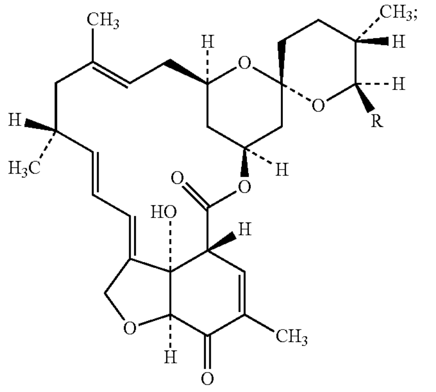

(2) oximation reaction: reacting the Milbemycin ketone with a hydroxylamine hydrochloride oximation agent in a methyl alcohol and 1,4-dioxane reaction solvent for 10-16 hours at 25-35° C. to obtain Milbemycin oxime

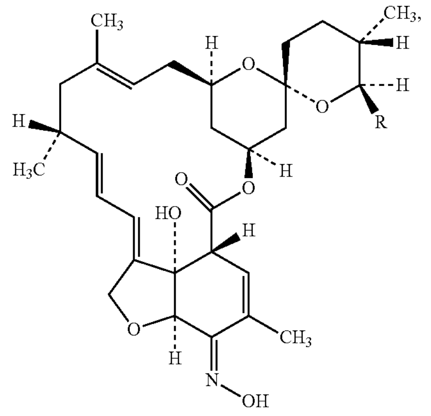

wherein R is methyl or ethyl.

2. The method for synthesizing Milbemycin oxime according to claim 1, wherein a mole ratio of the catalyst and Milbemycins is 0.05-0.4:1.

3. The method for synthesizing Milbemycin oxime according to claim 1, wherein the oxidizer used in step (1) is selected from a group consisting of sodium hypochlorite, calcium hypochlorite, and sodium chlorite; a mole ratio of oxidizer and Milbemycins is 3.5-35:1, wherein the oxidizer is dissolved into a solution by saturated sodium bicarbonate solution, wherein a mass percent concentration of the oxidizer in the solution is 0.5%-10%, wherein a pH value of the solution is controlled in a range of 8.5-11.5, wherein the solution is added dropwise into the reaction solution in 4-8 batches, and wherein a dropwise interval between each batch is 10-20 min.

4. The method for synthesizing Milbemycin oxime according to claim 1, wherein the catalyst promoter used in step (1) is selected from a group consisting of potassium iodide, sodium bromide, and sodium chloride; and wherein a mole ratio of catalyst promoter and Milbemycins is 0.05-0.4:1.

5. The method for synthesizing Milbemycin oxime according to claim 1, wherein the intermediate product Milbemycin ketone of step (1) is produced by first using a sodium thiosulfate solution to quench the reaction; adding methyl alcohol, keeping solution still for stratification; drying organic phase by anhydrous magnesium sulfate, after being centrifuged under a reduced pressure; and evaporating to obtain an intermediate product Milbemycin ketone, wherein a mole ratio of sodium thiosulfate and Milbemycins is 10-35:1, and the amount of methyl alcohol added is 10-30% of total volume of the reaction system.

6. The method for synthesizing Milbemycin oxime according to claim 1, wherein in step (2), a mass ratio of oximation agent hydroxylamine hydrochloride and Milbemycins is 1-1.5:1; wherein in the reaction solvent, a mass-to-volume ratio of methyl alcohol and 1,4-dioxane and Milbemycins is, methyl alcohol:1,4-dioxane:Milbemycins=(8-12 L):(10-16 L):1 Kg.

* * * * *